(12) United States Patent
Weyl et al.

(10) Patent No.: US 7,981,622 B2
(45) Date of Patent: Jul. 19, 2011

(54) PROCEDURE FOR THE DETERMINATION OF THE REACTION LAG PHASE IN AN ANALYTE-DEPENDENT REACTION

(75) Inventors: Andreas Weyl, Münchhausen (DE); Thilo Henckel, Rosebergstr (CH)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 245 days.

(21) Appl. No.: 12/081,470

(22) Filed: Apr. 16, 2008

(65) Prior Publication Data

US 2008/0261254 A1    Oct. 23, 2008

(30) Foreign Application Priority Data

Apr. 17, 2007 (DE) .................. 10 2007 017 906

(51) Int. Cl.
*G01N 33/53* (2006.01)
*G01N 33/557* (2006.01)
*G01N 33/86* (2006.01)

(52) U.S. Cl. ............................ 435/7.1; 436/517; 436/69

(58) Field of Classification Search .................. None
See application file for complete search history.

(56) References Cited

U.S. PATENT DOCUMENTS

| | | | |
|---|---|---|---|
| 3,458,287 A | | 7/1969 | Gross et al. |
| 3,881,992 A | * | 5/1975 | Ralston ............................. 435/3 |
| 4,217,107 A | | 8/1980 | Saito et al. |
| 4,252,536 A | | 2/1981 | Kishimoto et al. |
| 4,289,498 A | * | 9/1981 | Baughman et al. ............. 436/34 |
| 4,420,564 A | | 12/1983 | Tsuji et al. |
| 5,981,285 A | | 11/1999 | Carroll et al. |
| 6,044,330 A | | 3/2000 | Patzke |
| 6,245,569 B1 | | 6/2001 | Meyers |
| 2003/0044826 A1 | | 3/2003 | Ward et al. |
| 2004/0126832 A1 | | 7/2004 | Wang et al. |
| 2006/0121617 A1 | | 6/2006 | Henckel et al. |

FOREIGN PATENT DOCUMENTS

| | | |
|---|---|---|
| DE | 1 598 788 | 1/1971 |
| DE | 28 42 578 C2 | 4/1979 |
| DE | 28 48 552 C2 | 5/1979 |
| DE | 196 40 121 A1 | 4/1998 |
| EP | 0 420 332 B1 | 4/1991 |
| EP | 1 041 158 A2 | 10/2000 |
| EP | 1 316 802 A2 | 6/2003 |
| EP | 1 669 761 A2 | 6/2006 |
| WO | WO 2006/099255 A2 | 9/2006 |
| WO | WO 2007/002316 A2 | 1/2007 |

OTHER PUBLICATIONS

Panteleev et al. Spatial Propagation and Localization of Blood Coagulation Are Regulated by Intrinsic and Protein C Pathways, Respectively; Biophysical Journal, vol. 90 (2006) pp. 1489-1500.*

Zwietering et al. Comparison of Definitions of the Lag Phase and the Exponential Phase in Bacterial Growth; Journal of Applied Bacteriology, vol. 72 (1992) pp. 139-145.*

* cited by examiner

*Primary Examiner* — Rebecca Prouty
*Assistant Examiner* — Paul Martin
(74) *Attorney, Agent, or Firm* — Finnegan, Henderson, Farabow, Garrett & Dunner, L.L.P.

(57) ABSTRACT

The invention is in the field of analytical technique and relates to an improved procedure for determining the concentration or activity of an analyte, an analyte-dependent detection reaction being set in motion and the reaction kinetics determined being evaluated. The procedure makes possible an individual determination of the lag phase of the reaction kinetics for each measurement.

15 Claims, 3 Drawing Sheets

PROCEDURE FOR THE DETERMINATION OF THE REACTION LAG PHASE IN AN ANALYTE-DEPENDENT REACTION

This application claims benefit under 35 U.S.C. §119 (a)-(d) based on German Application No. 10 2007 017 906.7, filed Apr. 17, 2007, which is incorporated herein by reference in its entirety.

The invention is in the field of analytical technology and relates to an improved procedure for determining the concentration or activity of an analyte in a sample.

In modern analytical technology, depending on the type of analyte to be determined, a large number of different procedural principles are used. In order, for example, to detect proteins or peptides quantitatively or to determine them qualitatively, immunochemical procedures are preferably used. For this, antibodies are customarily used which specifically recognize the analyte. In order, for example, to detect an enzyme, labeled substrates are employed which are specifically modified by the enzyme to be detected. In order to obtain particularly meaningful and accurate results, it is often necessary to observe a test reaction over a period of time and to analyze its course. The change in a reaction-dependent measured variable over time is also designated as the reaction kinetics or signal-time curve. Various parameters of a curve of this type can be used for the evaluation and thus for the determination of the concentration or activity of an analyte.

Examples of detection reactions whose reaction kinetics are evaluated are, for example, particle-enhanced agglutination assays, in which particle-bound bi- or polyvalent antibodies react with an antigen, to form strongly light-scattering molecular aggregates. The analyte-dependent formation of these molecular aggregates can be measured by means of the measurement of the scattered light intensity (nephelometry) or via the measurement of the transmission increase or decrease (turbidimetry) and are used for the determination of the concentration of the analyte. Further examples are enzyme-based test procedures, in which the reaction of a chromogenic substrate is measured over time. The analyte-dependent cleavage of a chromogenic substrate can be measured, for example, via the measurement of the transmission increase or decrease at a certain wavelength and used for the determination of the concentration or activity of the analyte. Another example is clotting tests in which the activity of a single or a number of blood clotting factors is determined by the measurement of the fibrin formation rate in a blood or plasma sample. Typical examples of such clotting tests are the prothrombin time (PT), which is also called the Quick test or thromboplastin time, the activated partial thromboplastin time (APTT), the thrombin time (TT), the batroxobin time (BT) or the ecarin time (ECT).

Various parameters of reaction kinetics (signal-time curves) can be used for an evaluation. Known parameters are, for example, the maximum reaction rate or the time of occurrence of the maximum reaction rate. Often, for the evaluation of reaction kinetics the first or second derivative of the kinetics is also initially formed. A further known parameter of reaction kinetics, for example, is also the area under the first derivative of a signal-time curve. In other cases, the time is determined at which the signal exceeds a predetermined threshold value, or the signal level is determined which is achieved at a predetermined time. The further course of the reaction curve is then primarily evaluated for checking the plausibility of the measurements.

In the simplest case of a procedure for the determination of an analyte, a sample which contains the analyte is mixed with a reagent which contains the components necessary for the detection of the analyte, such as, for example, a substrate, a binding partner, an activator or the like. Customarily, the reaction is monitored from addition of the reagent, i.e. from the time to, by means of the measurement of a suitable physical signal. Ideally, the measurement signal behaves proportionally to the reaction at each point in time. Actually, however, various phenomena occur, such as, for example, inaccuracies in the measuring instrument, which lead to each absolute measurement signal not behaving proportionally to the reaction. Customarily, therefore, various smoothing procedures, for example, are used in order to obtain smoother reaction kinetics.

Another problem in the evaluation of reaction kinetics and thus in the determination of the concentration or activity of an analyte is the fact that immediately after the addition of a reagent to the sample variations and irregularities in the initial reaction course frequently occur that delay the start of the reaction before the exponential reaction phase. The exponential reaction phase is characterized by a relatively steep and constantly increasing course of the curve, that is a high reaction rate, and which in general represents the analytically most important reaction section. The first reaction phase, however, which is also designated as the reaction lag phase, is characterized by a flat course of the curve, that is a low reaction rate, and is usually not suitable for evaluation.

In the prior art, in many evaluation procedures a fixed time span $t_0$ to $t_n$, which should certainly comprise the reaction lag phase, is excluded from the evaluation from the start. Customarily, the duration of this period of time is determined for a specific test procedure by empirical investigations. For this, an adequate number of measurements are carried out under the necessary test conditions. In practice, it has been shown, however, that the duration of the reaction lag phase is variable even under constant test conditions. The disadvantage of the use of a fixed period of time $t_0$ to $t_n$, which should certainly comprise the reaction lag phase, consists in the fact that in cases in which the reaction lag phase is actually shorter, parts of the reaction kinetics which would be suitable for the evaluation cannot be used, whereas in cases in which the reaction lag phase is actually longer, parts of the reaction kinetics which are not suitable for the evaluation are used. In both cases, the danger exists of inaccuracies in the evaluation of the reaction kinetics and thus the danger of an erroneous determination of the analyte.

The present invention was also based on the object of making available a procedure for the determination of the concentration or activity of an analyte, which makes possible the specific determination of the reaction lag phase of reaction kinetics and thus guarantees a more accurate evaluation of the reaction kinetics and thus a more accurate determination of an analyte.

The object is achieved according to the invention by a procedure as claimed in claim 1.

The present invention relates to method of determining the concentration or activity of an analyte in a sample, the method comprising:
 a) mixing a sample with at least one reagent, whereby an analyte-dependent reaction is set in motion;
 b) measuring a signal (x) changing over time (t) as a result of the analyte-dependent reaction and storing of a resulting signal-time curve;
 c) determining a maximum increase in the signal-time curve;
 d) determining a reaction lag phase of the signal-time curve;

e) determining a concentration or an activity of the analyte by means of at least one parameter of the signal-time curve wherein the parameter occurs after the reaction lag phase in terms of time, where determining the reaction lag phase includes determining the period of time from the time of the first signal ($t_0$) up to the time $t_{lag}$. For this, a time $t_{max}$ of the maximum increase in the signal-time curve is first determined. Subsequently—starting from the time $t_{max}$—the time $t_{lag}$ is determined, where $t_{lag}$ is smaller than $t_{max}$, i.e. is before $t_{max}$ in terms of time and where $t_{lag}$ corresponds to the time at which the increase in the signal-time curve—starting from $t_{max}$—falls short of a threshold value for the first time. The threshold value corresponds to a test-specific, predetermined fraction of the maximum increase in the signal-time curve. Preferentially, the threshold value corresponds to a proportion of 1 to 45% of the maximum increase in the signal-time curve.

The measurement of the signal (x) changing over time (t) as a result of the analyte-dependent reaction is carried out with the aid of suitable detection devices. The signal can be any type of signal known to the person skilled in the art, such as, for example, optical properties of the reaction batch (e.g. turbidity, light scattering, fluorescence, chemiluminescence), chemical properties of the reaction batch (e.g. pH, redox potential, viscosity, strength) or electrochemical properties (e.g. conductivity, impedance, resistance).

The measurement over time (t) is customarily carried out by means of the continuous detection of the physical signal, preferably at regular time intervals, such as, for example, one measurement per second. The signal-time curve thus obtained is stored in order to be available for the subsequent evaluation. The term "signal-time curve" is to be broadly understood in this connection and not restricted to the graphic representation of a corresponding curve. On the contrary, the assignment of the measured values to the accompanying times in an ordered series is meant thereby.

The determination of the maximum increase in the signal-time curve can be carried out by any desired procedure known to the person skilled in the art, but preferentially by first forming the 1st derivative of the signal-time curve and determining the maximum of the 1st derivative. The time of the maximum of the 1st derivative corresponds to the time $t_{max}$ of the maximum increase in the signal-time curve.

The determination of the time $t_{lag}$, which defines the end of the reaction lag phase, is carried out by searching for the time, starting from $t_{max}$ in the signal-time curve, at which the increase in the signal-time curve for the first time falls short of a threshold value, this time having to be smaller than $t_{max}$, i.e. having to be before $t_{max}$ in terms of time. The fact that, starting from $t_{max}$, the time is sought at which the increase in the signal-time curve for the first time falls short of a threshold value has the advantage that possible extreme variations entirely at the start of the measured value recording cannot lead to a wrong determination of the reaction lag phase. If, starting from $t_0$, the time is sought at which the increase in the signal-time curve exceeds a threshold value for the first time, an extreme variation of this type, which can occasionally occur entirely at the start of the measurement on account of mixing procedures between the sample and reagent, could lead to the determination of a reaction lag phase which is wrongly too short (see, for example, FIG. 3).

The threshold value corresponds to a test-specific, predetermined fraction of the maximum increase in the signal-time curve. Which fraction of the maximum increase in the signal-time curve is suitable for a certain test procedure can be determined empirically beforehand by a simple series of tests. If the reaction lag phase calculated with the aid of a preliminary threshold value and the expected reaction lag phase agree and this agreement can be confirmed in a large number of sample measurements, a suitable threshold value has been found. Preferentially, the threshold value is chosen such that it corresponds to a proportion of 1 to 45% of the maximum increase in the signal-time curve. Generally, it can be said that for the threshold value, a smaller fraction of the maximum increase in the signal-time curve is to be chosen the more steeply the signal-time curve customarily increases in a certain test procedure.

After the beginning and end of the reaction lag phase ($t_0$-$t_{lag}$) have been determined, the determination of the concentration or activity of the analyte is carried out by means of at least one parameter of the signal-time curve, which lies after the reaction lag phase in terms of time.

A "sample" in the sense of the invention is to be understood as meaning a material which presumably contains the substance to be detected, i.e. the analyte. The term "sample" comprises, for example, biological fluids or tissue, in particular of humans and animals, such as blood, plasma, serum, saliva, sputum, exudate, bronchioalveolar lavage, lymph fluid, synovial fluid, seminal fluid, vaginal mucus, feces, urine, cerebrospinal fluid, hair, skin, tissue samples or sections. Cell culture samples, plant fluids or tissue, forensic samples, water and waste water samples, food and medicaments are furthermore included. If appropriate, the samples must be pretreated in order to make the analytes accessible for the detection procedure or in order to remove interfering sample constituents. Pretreatment of samples of this type may comprise the separation and/or lysis of cells, the precipitation, the hydrolysis or the denaturation of sample constituents, such as, for example, proteins, the centrifugation of samples, the treatment of the sample with organic solvents such as, for example, alcohols, in particular methanol; or the treatment of the sample with detergents. Often, the sample is transferred to another, usually aqueous medium, which if possible should not interfere with the detection procedure.

The term "analyte" is to be understood in the sense of the invention as meaning the substance to be detected (for examples of the term "analyte" see EP 515 194 A2, pages 8-15) or alternatively a biological parameter which gives information about the state of a physiological process or of a multistage, multifactoral reaction system. Examples of such biological parameters are, for example, the various known clotting times, such as, for example, the prothrombin time (PT) or the activated partial thromboplastin time (APTT), which yield information about the various parts of the blood clotting cascade or of the fibrinolysis system.

In preferred embodiments of the procedure according to the invention, the analyte-dependent reaction is an antigen-antibody reaction or an enzyme-substrate reaction.

Procedures are furthermore preferred in which the analyte-dependent reaction is the formation of a fibrin clot in a whole blood or plasma sample.

A procedure according to the invention for the determination of the concentration or activity of thrombin, preferably of endogenous thrombin, is particularly preferred. For this, the sample is customarily mixed with a reagent for the activation of prothrombin to thrombin. In order to induce thrombin information, it is possible to use, for example, solutions which contain $Ca^{2+}$ ions and additionally, for example, thromboplastin or a contact activator, such as, for example, kaolin, phospholipids, snake venom, or thrombomodulin and activated protein C. Depending on the diagnostic problem, the person skilled in the art can choose from the large number of known activators of blood clotting in order to consider either a part of or the entire clotting system. The measurement of the conversion kinetics of a thrombin substrate necessary for the determination of endogenous thrombin requires that the sample to be investigated is treated with a thrombin substrate, that thrombin formation is induced, e.g. by addition of a thrombin formation activator, and that a physical or chemical property of the thrombin substrate reacted is measured as a function of time (see also EP 420 332 B1).

Suitable thrombin substrates are, for example, oligopeptides which are composed of a part which comprises a specific recognition sequence for thrombin, and of a leaving signal group having a measurable physical property. The leaving signal group, which preferentially has a modified physical property after cleavage, can be, for example, a chromophoric, chemiluminescent or fluorescent group whose property can be measured. Chromophoric signal groups are preferred whose optical property is determined photometrically, such as, for example, para-nitroanilide (pNA), whose absorption can be measured at a wavelength of 405 nm after cleavage by thrombin.

Preferentially, the determination of the concentration or activity of endogenous thrombin is carried out by means of the "endogenous thrombin potential" (ETP). For this, after the reaction lag phase has been determined, the area under the first derivative of the signal-time curve is determined. A particularly preferred variant of the determination of the endogenous thrombin potential is described in EP 1 669 761 A2.

The invention further relates to an apparatus which is capable of automatically carrying out the method according to the invention for determining the activity or concentration of an analyte. An apparatus of this type is distinguished in that it has a) means for the determination of the signal (x) changing over time (t) as a result of the analyte-dependent reaction (e.g. a photometer, pH meter, dosimeter, luminometer, fluorimeter or the like), b) means for storing the signal-time curve (e.g. a semiconductor memory, an optical or magnetic storage medium such as, for example, a hard disk), c) means for determining the time $t_{max}$ of the maximum increase in the stored signal-time curve (e.g. software, computer program, algorithm) and means for controlling the implementation of the step of determining of a time $t_{lag}$ (e.g. software, computer program, algorithm). Preferentially, the apparatus additionally has means for the output of measurement results (e.g. an electronic display unit, a monitor, a data recorder, a printer and/or data transmission line).

The examples described below serve for the exemplary illumination of individual aspects of this invention and are not to be understood as a restriction:

EXAMPLES

Various known test procedures for the determination of various analytes in human plasma samples were carried out in an automatic clotting analyzer (BCS® system, Dade Behring Marburg GmbH, Marburg, Germany). Software was additionally installed on the apparatus, which made possible the automatic implementation of the procedure according to the invention for the determination of the reaction lag phase.

Figure 1:
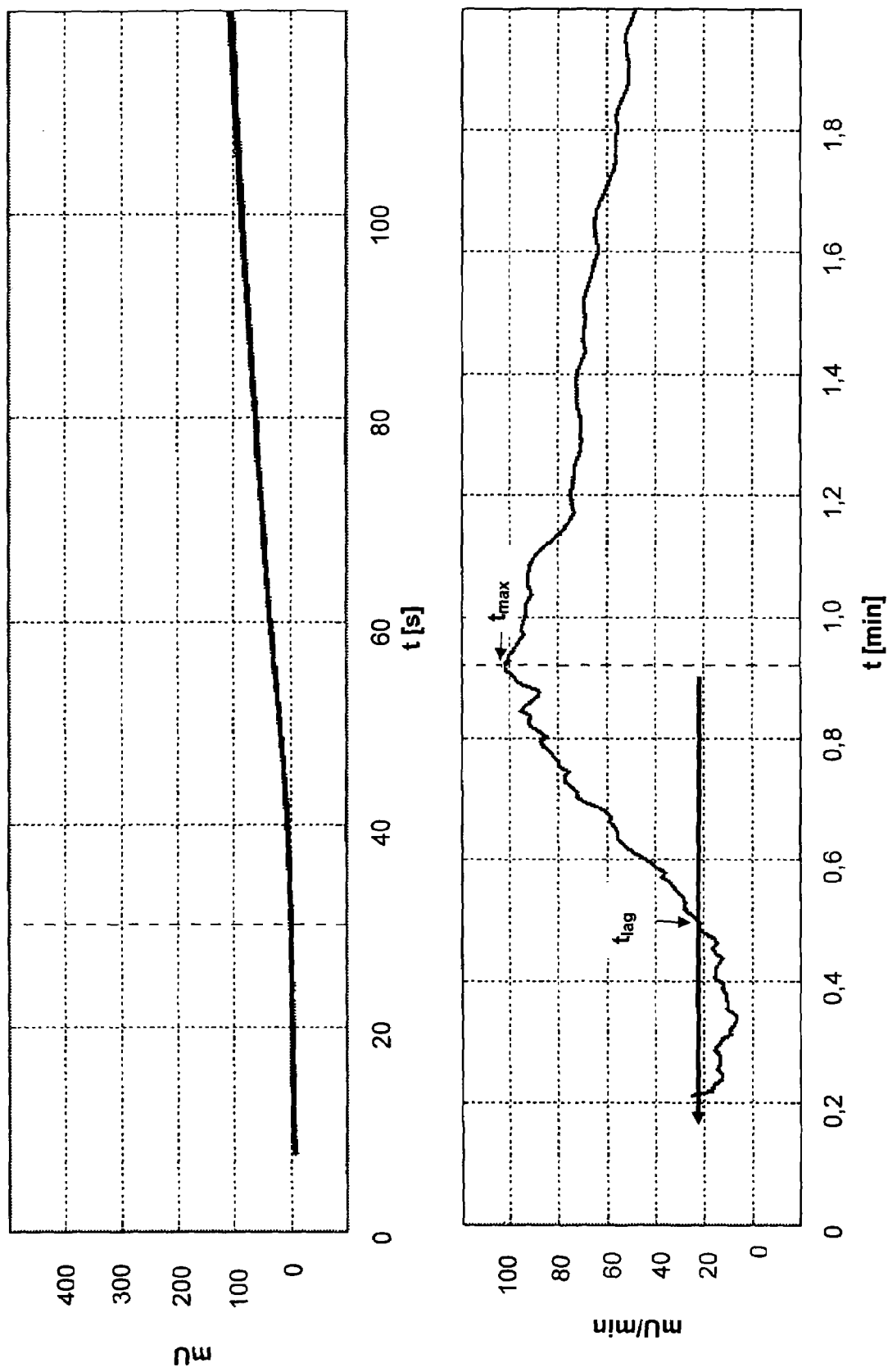
FIG. 1 Determination of the reaction lag phase of a signal-time curve of a thrombin generation reaction in a plasma sample, which was started by addition of Innovin®. The upper diagram shows the measured values [mU] over time. The dashed vertical line marks the time $t_{lag}$. The lower diagram shows the 1st derivative of these reaction kinetics. The dashed vertical line marks the time of the maximum of the 1st derivative, which corresponds to the time $t_{max}$ of the maximum increase in the signal-time curve. The maximum of the 1st derivative is $c_{max}=102.86$ mU/min. For the threshold value, 20% of the maximum signal of the 1st derivative had been determined in advance. The threshold value resulting therefrom of 20.572 mU/min (solid horizontal line), starting from $t_{max}$, is fallen short of for the first time at 0.503 min (=30.2 s). This time corresponds to $t_{lag}$.
Figure 2:
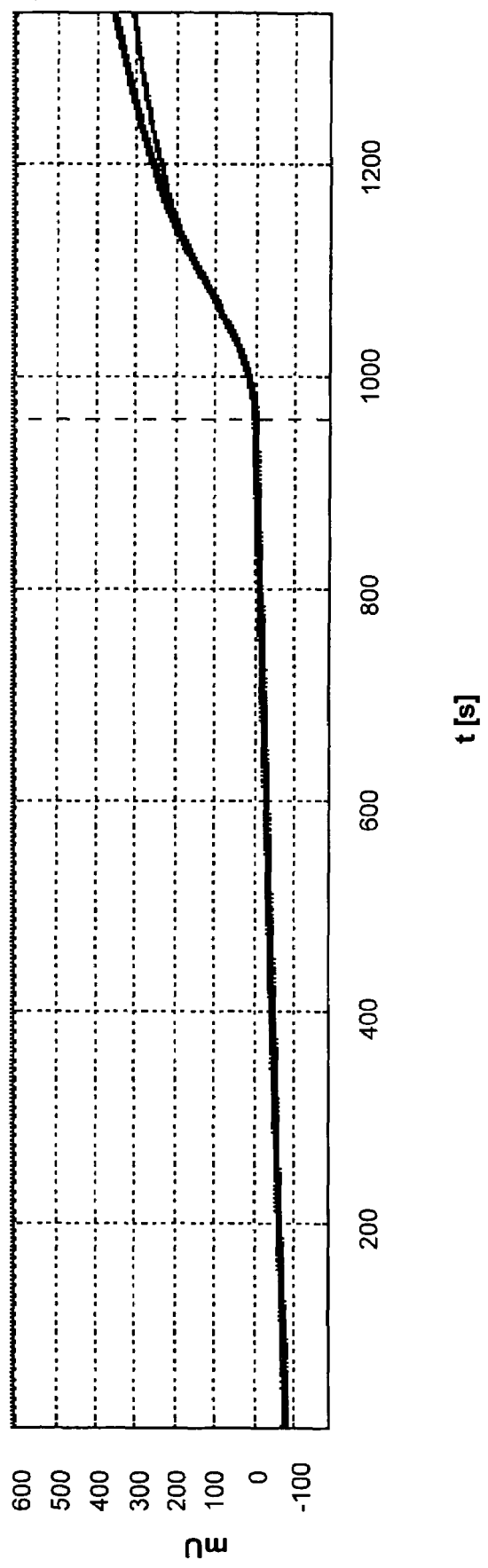
FIG. 2 Determination of the reaction lag phase of a signal-time curve of a thrombin generation reaction in a plasma sample, which was started by addition of Actin® FS. The dashed vertical line marks the time $t_{lag}$ at 960.2 seconds.

For the determination of thrombin generation, a plasma sample was mixed with a para-nitroanilide-coupled thrombin-specific peptide substrate, and the thrombin generation was started by addition of Innovin® (reagent consisting of recombinant, human tissue factor and a mixture of synthetic phospholipids; Dade Behring Marburg GmbH, Marburg, Germany) and $CaCl_2$ or by addition of Actin® FS (APTT reagent, Dade Behring Marburg GmbH, Marburg, Germany) and $CaCl_2$. The reaction kinetics are shown in FIG. 1 and FIG. 2. FIG. 1 here shows the enlarged section of the first 100 seconds measurement time. The total measurement times were 20 minutes in the case of activation with Innovin®, and 50 minutes in the case of activation with Actin® FS. The lag phase was 30.2 seconds when using Innovin® (FIG. 1) and 960.2 seconds when using Actin® FS (FIG. 2).

Figure 3:
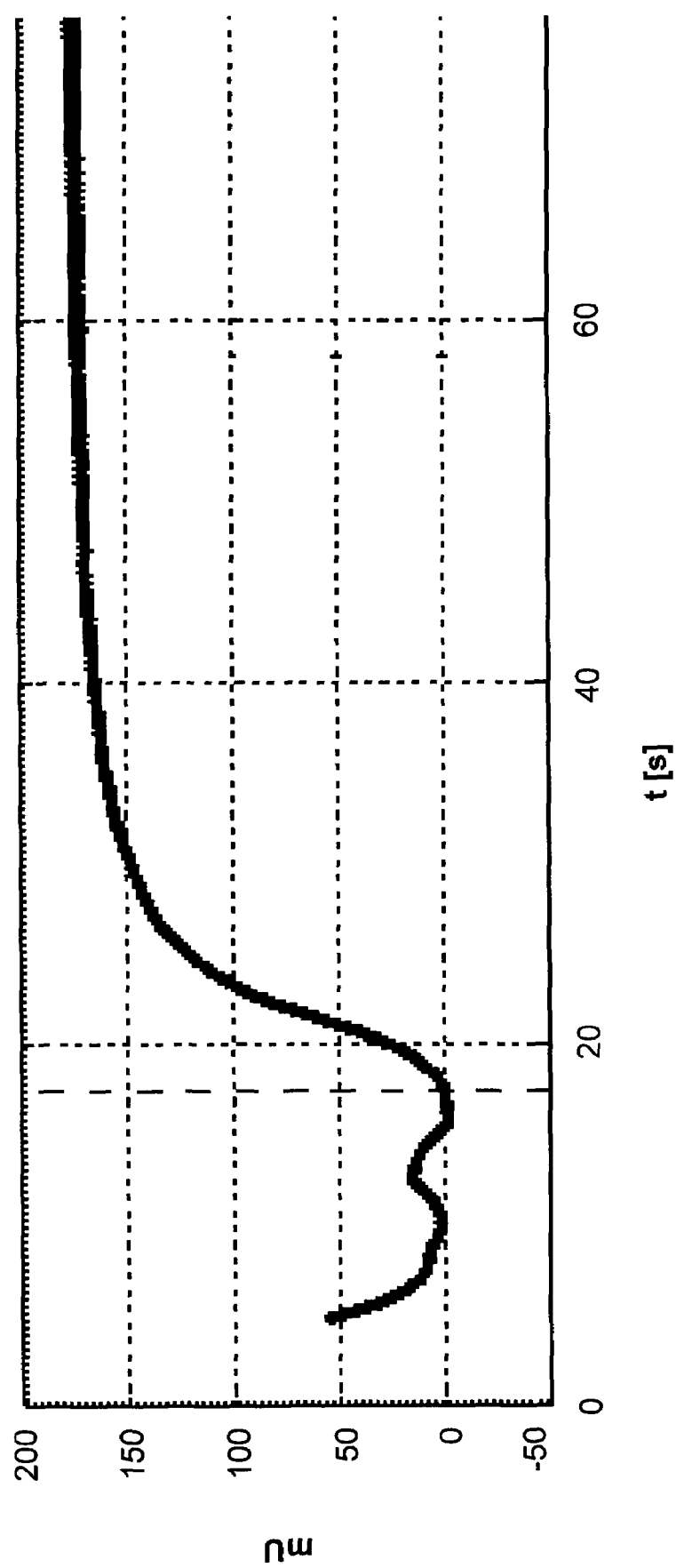
FIG. 3 Determination of the reaction lag phase of a signal-time curve of a prothrombin time clotting reaction in a plasma sample, which was started by addition of Innovin®. The dashed vertical line marks the time $t_{lag}$ at 17.3 seconds.

For the determination of the prothrombin time (PT), a plasma sample was mixed with Innovin® according to the manufacturer's instructions. The total measurement period was 120 seconds. The lag phase was determined at 17.3 seconds. The procedure according to the invention for determination of the lag phase behaves robustly to signal disturbances and signal noise at the beginning of the measurement and evaluates the lag phase correctly (FIG. 3).

The invention claimed is:

1. A method for determining the concentration or activity of an analyte in a sample, the method comprising:
   mixing a sample with at least one reagent, whereby an analyte-dependent reaction is set in motion;
   measuring a signal (x) changing over time (t) as a result of the analyte-dependent reaction and storing a resultant signal-time curve;
   determining a maximum increase in the signal-time curve; determining a reaction lag phase of the signal-time curve; and determining a concentration or activity of the analyte by means of at least one parameter of the signal-time curve, wherein the parameter occurs after the reaction lag phase in terms of time, and
      wherein determining the reaction lag phase includes determining a period of time from a time of a first signal ($t_0$) up to a time $t_{lag}$;
      by determining a time $t_{max}$ of the maximum increase in the signal-time curve; and
      subsequently determining from the time $t_{max}$, the time $t_{lag}$, where $t_{lag}$ is smaller than $t_{max}$ and where $t_{lag}$ corresponds to the time at which the increase in the signal-time curve for the first time reaches a threshold value and where the threshold value corresponds to a test-specific, predetermined fraction of the maximum increase in the signal-time curve.

2. The method of claim 1, wherein the threshold value corresponds to a fraction of 1 to 45% of the maximum increase in the signal-time curve.

3. The method of claim 1, wherein determining the concentration or activity of an analyte includes determining the concentration or activity of an analyte in a biological sample selected from the group consisting of whole blood, plasma, serum, urine, feces, saliva or cerebrospinal fluid.

4. The method of claim 1, wherein the analyte-dependent reaction is an antigen-antibody reaction or an enzyme-substrate reaction.

5. The method of claim 1, wherein measuring a signal (x) includes measuring a signal selected from the group consisting of scattered light, turbidity, fluorescence and chemiluminescence.

6. The method of claim 1, wherein the method for determining the concentration or activity of an analyte includes determining the concentration or activity of thrombin.

7. The method of claim 6, further comprising mixing the sample with a reagent for the activation of prothrombin to thrombin.

8. The method of claim 7, where the sample is mixed with a reagent comprising a thrombin substrate.

9. The method of claim 8, wherein measuring the signal (x) changing over time (t) includes measuring a signal (x) changing over time (t) as a result of the thrombin-dependent substrate cleavage and storing the resulting signal-time curve.

10. The method of claim 6, wherein the method for determining the concentration or activity of thrombin further comprises determining the formation and inhibition of endogenous thrombin.

11. The method of claim 1, further comprising determining a clotting time.

12. The method of claim 11, wherein determining the clotting time includes determining a clotting time selected from the group consisting of prothrombin time, activated partial thromboplastin time, thrombin time, batroxobin time and ecarin time.

13. The method of claim 1, wherein the at least one parameter is at least one of a maximum reaction rate, a time at which the maximum reaction rate occurs, an area under a first derivative of the signal-time curve, a time at which the signal (x) exceeds a predetermined signal, and a signal which is achieved at a predetermined time.

14. The method of claim 1, wherein the threshold value is determined by calculating a preliminary reaction lag phase and comparing the preliminary reaction lag phase to an expected lag phase over a number of tests.

15. The method of claim 1, wherein the maximum increase in the signal time curve is a slope of the signal time curve.

\* \* \* \* \*